US011208839B2

(12) United States Patent
Lee

(10) Patent No.: US 11,208,839 B2
(45) Date of Patent: Dec. 28, 2021

(54) SPACE VENTING UPWARD ACTING DOOR SYSTEM AND METHOD

(71) Applicant: GMI Holdings, Inc., Mount Hope, OH (US)

(72) Inventor: Bradley J. Lee, Arlington, TX (US)

(73) Assignee: GMI Holdings, Inc., Mount Hope, OH (US)

( * ) Notice: Subject to any disclaimer, the term of this patent is extended or adjusted under 35 U.S.C. 154(b) by 0 days.

(21) Appl. No.: 16/808,122

(22) Filed: Mar. 3, 2020

(65) Prior Publication Data

US 2021/0277702 A1    Sep. 9, 2021

(51) Int. Cl.
*E05F 15/72* (2015.01)
*G01N 33/00* (2006.01)
*G08B 21/14* (2006.01)

(52) U.S. Cl.
CPC .......... *E05F 15/72* (2015.01); *G01N 33/004* (2013.01); *G08B 21/14* (2013.01); *E05Y 2400/44* (2013.01); *E05Y 2800/416* (2013.01); *E05Y 2800/42* (2013.01); *E05Y 2900/106* (2013.01); *E05Y 2900/132* (2013.01)

(58) Field of Classification Search
None
See application file for complete search history.

(56) References Cited

U.S. PATENT DOCUMENTS

| | | | | | |
|---|---|---|---|---|---|
| 3,826,180 A | * | 7/1974 | Hayashi | ................... | A62C 2/06 454/342 |
| 4,197,675 A | * | 4/1980 | Kelly | ...................... | E05F 15/72 340/634 |
| 4,360,801 A | * | 11/1982 | Duhame | .............. | G08B 17/117 318/16 |
| 4,647,714 A | * | 3/1987 | Goto | ...................... | B32B 15/04 174/36 |
| 5,125,505 A | * | 6/1992 | Kurosaki | .................. | G09F 3/18 206/39.4 |
| 5,365,217 A | * | 11/1994 | Toner | ................... | G08B 25/009 340/531 |
| 5,828,292 A | * | 10/1998 | Kokhan | ............... | G08B 25/016 340/307 |

(Continued)

FOREIGN PATENT DOCUMENTS

| | | | | |
|---|---|---|---|---|
| JP | 2003064648 A | * | 3/2003 | |
| JP | 2013096190 A | * | 5/2013 | |
| KR | 20050001595 A | * | 1/2005 | |

*Primary Examiner* — Fekadeselassie Girma
(74) *Attorney, Agent, or Firm* — Haynes and Boone, LLP

(57) ABSTRACT

A door operator includes: a controller; a sensor operatively connected to the controller, the sensor configured to detect an undesirable condition and communicate a signal to the controller when the undesirable condition is detected; and a door operatively connected to the controller, the controller is configured to cause the door to move from a closed position to a non-closed position when the controller receives the signal. In another aspect, the disclosure describes a method of operating a door. The method includes: detecting an undesirable condition with a sensor; communicating with a controller when the undesirable condition is detected by the sensor; and moving the door from a closed position to a non-closed position when the controller receives the signal.

18 Claims, 2 Drawing Sheets

(56) References Cited

U.S. PATENT DOCUMENTS

| | | | | |
|---|---|---|---|---|
| 6,121,544 A * | 9/2000 | Petsinger | G06K 19/005 | |
| | | | 150/147 | |
| 6,127,938 A * | 10/2000 | Friedman | G07B 15/063 | |
| | | | 206/720 | |
| 6,155,410 A * | 12/2000 | Davis | A45C 11/182 | |
| | | | 150/147 | |
| 6,845,863 B1 * | 1/2005 | Riley | A45C 11/182 | |
| | | | 150/147 | |
| 7,183,933 B2 | 2/2007 | Dzurko et al. | | |
| 7,243,840 B2 * | 7/2007 | Bason | G06K 19/025 | |
| | | | 235/375 | |
| 7,635,089 B2 * | 12/2009 | Augustinowicz | G06K 19/07327 | |
| | | | 235/486 | |
| 7,710,284 B2 | 5/2010 | Dzurko et al. | | |
| 7,980,458 B2 * | 7/2011 | Kon | G06Q 20/10 | |
| | | | 235/375 | |
| 8,038,068 B2 * | 10/2011 | Yuzon | G07F 7/1016 | |
| | | | 235/492 | |
| 8,212,653 B1 * | 7/2012 | Goldstein | G08B 21/245 | |
| | | | 340/10.1 | |
| 8,578,982 B2 * | 11/2013 | Lee | G06K 19/07327 | |
| | | | 150/147 | |
| 8,604,995 B2 * | 12/2013 | Hammad | G06F 1/1698 | |
| | | | 343/841 | |
| 8,669,878 B1 * | 3/2014 | Vantilburg | E06B 9/68 | |
| | | | 340/632 | |
| 8,723,675 B2 * | 5/2014 | Augustinowicz | G06K 19/005 | |
| | | | 340/572.8 | |
| 8,763,913 B2 * | 7/2014 | Alo | G06K 19/07327 | |
| | | | 235/492 | |
| 8,803,696 B1 * | 8/2014 | Dunyan | E05F 15/689 | |
| | | | 340/632 | |
| 9,135,478 B2 * | 9/2015 | Burns | G06K 7/0021 | |
| 9,265,331 B1 * | 2/2016 | Hoffman | A45F 5/00 | |
| 9,300,581 B1 * | 3/2016 | Hui | H04L 61/2015 | |
| 9,613,353 B1 * | 4/2017 | Quigley | G06Q 20/405 | |
| 9,697,453 B2 * | 7/2017 | Augustinowicz | G06K 19/07318 | |
| 9,726,750 B2 * | 8/2017 | Gross | G01S 19/48 | |
| 10,373,503 B2 * | 8/2019 | Wright | G08G 1/163 | |
| 10,424,193 B1 * | 9/2019 | Schueler | H04B 1/38 | |
| 10,475,323 B1 * | 11/2019 | Ross | H04W 4/14 | |
| 2002/0177471 A1 * | 11/2002 | Kaaresoja | G08B 6/00 | |
| | | | 455/567 | |
| 2004/0148837 A1 * | 8/2004 | Lewis | G09F 3/20 | |
| | | | 40/654.01 | |
| 2005/0212681 A1 * | 9/2005 | Dzurko | G08B 21/14 | |
| | | | 340/632 | |
| 2005/0237014 A1 * | 10/2005 | Murray | E05F 15/668 | |
| | | | 318/280 | |
| 2005/0262519 A1 * | 11/2005 | Luebke | G08B 13/19684 | |
| | | | 719/318 | |
| 2006/0017570 A1 * | 1/2006 | Moskowitz | G06K 19/07327 | |
| | | | 340/572.7 | |
| 2007/0247096 A1 * | 10/2007 | Tang | E05F 15/70 | |
| | | | 318/280 | |
| 2008/0121321 A1 * | 5/2008 | Tiner | A45C 13/02 | |
| | | | 150/131 | |
| 2009/0124189 A1 * | 5/2009 | Barber | F24F 11/0001 | |
| | | | 454/258 | |
| 2010/0171588 A1 * | 7/2010 | Chutorash | E05F 15/668 | |
| | | | 340/5.71 | |
| 2010/0201531 A1 * | 8/2010 | Pakravan | G08B 29/20 | |
| | | | 340/632 | |
| 2010/0265084 A1 * | 10/2010 | Augustinowicz | G06K 19/07741 | |
| | | | 340/686.6 | |
| 2011/0030639 A1 * | 2/2011 | Kwiecinski | F02N 11/0807 | |
| | | | 123/179.2 | |
| 2011/0068918 A1 * | 3/2011 | Cummings | G08B 21/02 | |
| | | | 340/540 | |
| 2011/0252597 A1 * | 10/2011 | Burris | E05F 3/22 | |
| | | | 16/52 | |
| 2011/0319048 A1 * | 12/2011 | Matlock | G08B 25/016 | |
| | | | 455/404.1 | |
| 2012/0079750 A1 * | 4/2012 | Lawrence | G09F 3/207 | |
| | | | 40/1.5 | |
| 2012/0228020 A1 * | 9/2012 | Winch | H05K 9/0043 | |
| | | | 174/378 | |
| 2012/0310547 A1 * | 12/2012 | Cristoforo | G01N 33/0073 | |
| | | | 702/24 | |
| 2013/0220842 A1 * | 8/2013 | Lazott | A45C 11/18 | |
| | | | 206/39.4 | |
| 2013/0306738 A1 * | 11/2013 | Peterson | H05B 47/105 | |
| | | | 235/492 | |
| 2014/0289844 A1 * | 9/2014 | Suwald | G06K 19/0719 | |
| | | | 726/20 | |
| 2014/0289845 A1 * | 9/2014 | Suwald | B42D 25/22 | |
| | | | 726/20 | |
| 2014/0380452 A1 * | 12/2014 | Suwald | G07C 9/257 | |
| | | | 726/9 | |
| 2015/0057981 A1 * | 2/2015 | Gross | G01S 19/48 | |
| | | | 703/1 | |
| 2015/0124089 A1 * | 5/2015 | Swallow | G08B 13/19632 | |
| | | | 348/143 | |
| 2015/0137942 A1 * | 5/2015 | Suwald | G06F 21/34 | |
| | | | 340/5.65 | |
| 2015/0156301 A1 * | 6/2015 | Crawford | H04M 1/72409 | |
| | | | 455/420 | |
| 2016/0053699 A1 * | 2/2016 | Ozkan | G01N 33/004 | |
| | | | 701/112 | |
| 2016/0134932 A1 * | 5/2016 | Karp | H04L 67/22 | |
| | | | 348/155 | |
| 2016/0240075 A1 * | 8/2016 | Eisenman | H04W 4/90 | |
| 2017/0079257 A1 * | 3/2017 | Haensgen | H04W 84/18 | |
| 2018/0112454 A1 * | 4/2018 | Preus | E05F 15/77 | |
| 2019/0095735 A1 * | 3/2019 | Shah | G06F 21/36 | |
| 2019/0096289 A1 * | 3/2019 | Harkness | G08B 21/02 | |
| 2019/0140892 A1 * | 5/2019 | Jain | H04L 41/16 | |
| 2019/0172333 A1 * | 6/2019 | Combe | G08B 21/16 | |
| 2019/0271185 A1 * | 9/2019 | Fitzgibbon | E05F 15/668 | |
| 2019/0278893 A1 * | 9/2019 | Eisen | G06F 3/03547 | |
| 2019/0390503 A1 * | 12/2019 | Teta | E05F 1/006 | |
| 2020/0080360 A1 * | 3/2020 | Hsieh | E05F 15/72 | |

* cited by examiner

SPACE VENTING UPWARD ACTING DOOR SYSTEM AND METHOD

TECHNICAL FIELD

This patent disclosure relates generally to an upward acting door system and method and, more particularly, to an upward acting door system and method that is configured to vent a space such as a garage, warehouse or other interior space.

BACKGROUND

Garages, warehouse spaces and other areas that are enclosed, or at least partially enclosed, by an upward acting door occasionally contain undesirable conditions. For example, the spaces may become too hot, particularly on a hot day and a vehicle is parked in the space. Heat from the engine may be transferred to the space raising the temperature to be hotter than the outside and bringing the temperature in the space to an uncomfortable level.

Other undesirable conditions may include the space containing undesirable substances such as carbon monoxide (CO), smoke, water or other liquid (flooding) and the like. Accordingly, it is desirable to have a system and method for mitigating undesirable conditions that may occur in an enclosed space.

SUMMARY

The foregoing needs are met to a great extent by embodiments in accordance with the present disclosure, wherein, in some embodiments includes a door operator. The door operator includes: a controller; a sensor operatively connected to the controller, the sensor configured to detect an undesirable condition and communicate a signal to the controller when the undesirable condition is detected; and a door operatively connected to the controller and the controller is configured to cause the door to move from a closed position to a non-closed position when the controller receives the signal.

In another aspect, the disclosure describes a method of operating a door. The method includes: detecting an undesirable condition with a sensor; communicating with a controller when the undesirable condition is detected by the sensor; and moving the door from a closed position to a non-closed position when the controller receives the signal.

In another aspect, the disclosure describes a door operator. The door operator includes: a controller; a sensor operatively connected to the controller, the sensor configured to detect any one of heat, liquid pooled on a floor, and CO and communicate a signal to the controller when any one of the heat, liquid, and CO is detected; and a door operatively connected to the controller, the controller is configured to cause the door to move from a closed position to an intermediate position between a closed position and a fully opened position and stop at the intermediate position when the controller receives the signal.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Additional features, advantages, and aspects of the disclosure may be set forth or apparent from consideration of the following detailed description, drawings, and claims. Moreover, it is to be understood that both the foregoing summary of the disclosure and the following detailed description are exemplary and intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate aspects of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings.

DETAILED DESCRIPTION

Figure 1:
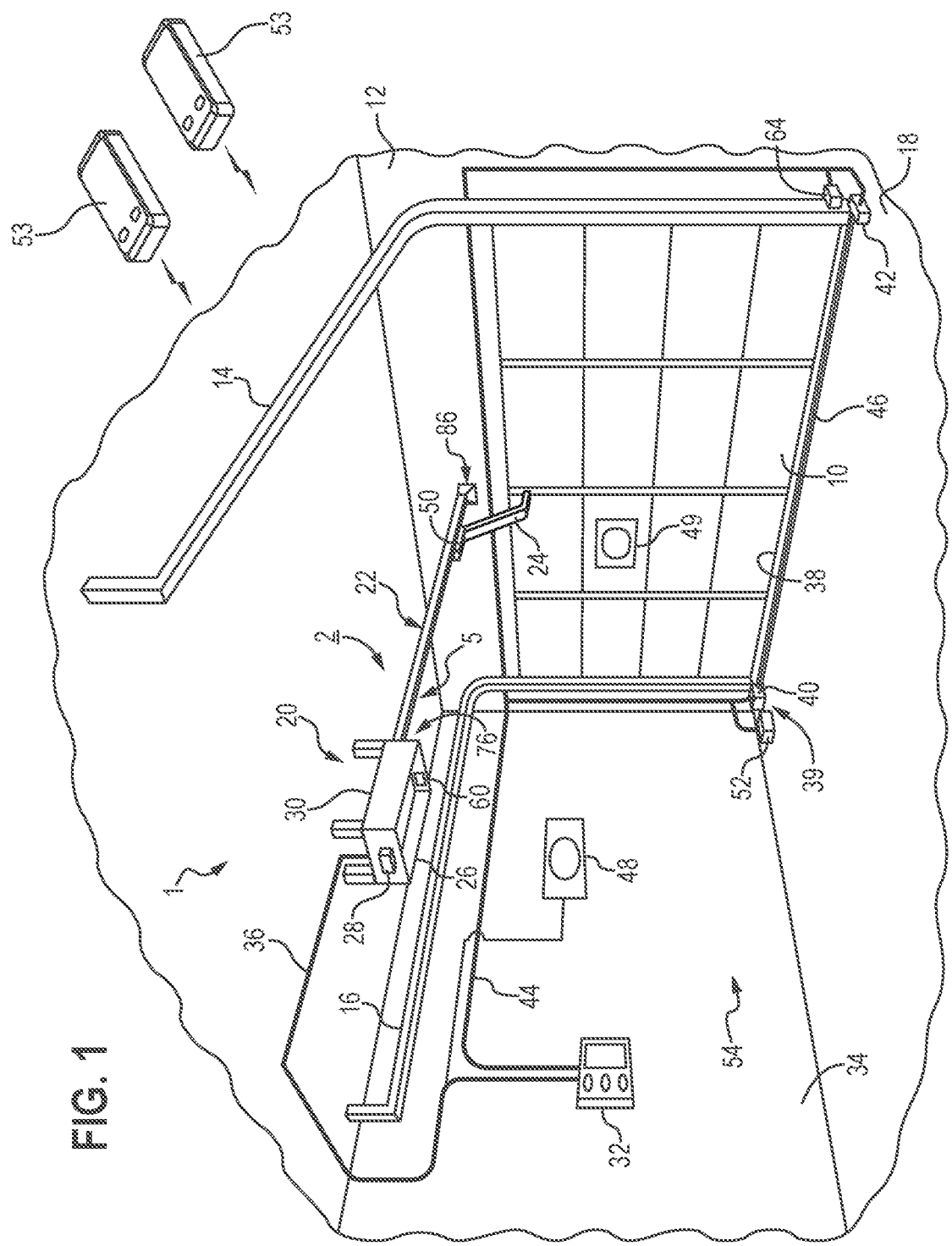
FIG. 1 is a perspective view of a type of space that can be vented with an upward acting door system in accordance with the present disclosure.

The aspects of the disclosure and the various features and advantageous details thereof are explained more fully with reference to the non-limiting aspects and examples that are described and/or illustrated in the accompanying drawings and detailed in the following description. It should be noted that the features illustrated in the drawings are not necessarily drawn to scale, and features of one aspect may be employed with other aspects as the skilled artisan would recognize, even if not explicitly stated herein. Descriptions of well-known components and processing techniques may be omitted so as to not unnecessarily obscure the aspects of the disclosure. The examples used herein are intended merely to facilitate an understanding of ways in which the disclosure may be practiced and to further enable those of skill in the art to practice the aspects of the disclosure. Accordingly, the examples and aspects herein should not be construed as limiting the scope of the disclosure, which is defined solely by the appended claims and applicable law. Moreover, it is noted that like reference numerals represent similar parts throughout the several views of the drawings.

Referring initially to FIG. 1, there is illustrated a garage door installation including a barrier operator system 1 for moving a barrier, which in this example is an upward acting sectional garage door 10. The door is movable along opposed sets of guide tracks 14 and 16 between a lowermost closed position, as shown, covering an opening in a wall 12, and an upwardmost open position, in which the door 10 would be parallel to the floor 18. In its closed position, the door 10 would typically be in sealing engagement with the floor 18 or at least in close proximity to such surface. Barrier operator 20 is disposed within a housing or head unit 26 and includes (i) an antenna and RF receiver unit (not shown) for receiving wireless transmissions and a (ii) microcontroller based controller unit 30 for, among other functions, processing the incoming wired and wireless transmitted door commands, and generating motor control signals corresponding to such commands to a DC or AC motor 28. As subsequently described in greater detail, and in accordance with a feature of the present invention, the controller unit 30 preferably comprises multiple microcontrollers under respective software control.

Specifically encrypted RF transmissions emanate from hand held (or vehicle mounted) transmitters 53 representing door commands to the barrier operator 20. Commands can also be transmitted from an interior wall mounted console 32, and/or an exterior wall mounted keyless entry console (not shown). The barrier operator 20 may be similar, for example, to that described in U.S. Pat. No. 6,118,243, issued Sep. 12, 2000 to Reed et al., and incorporated herein by reference for all purposes, but having the hereinafter described additions, modifications and features.

The barrier operator system 1 additionally includes a mechanical drive sub-system 2, the details of which are subsequently described, and generally comprises as its major components, (i) an elongated beam or rail assembly 22 connected at one end 86 to wall 12 and at its opposite end 76 to the barrier operator head unit or housing 26; (ii) a drive assembly 5, which can be a reciprocatingly driven drive belt or chain or a rotatably driven screw drive, supported by the rail assembly 22, and (iii) a carriage 50 operably connected to the drive assembly 5. The carriage 50 is disconnectably engageable with an arm 24 which, in turn, is firmly connected to the door 10. Accordingly, motor 28, under control of the barrier operator 20, drives the belt, chain or rotatable screw in one direction or the other, consequently transporting the carriage 50 to respectively raise (open) or lower (close) the door 10. A compression spring and trained cables assembly (not shown) is connected with the door 10 so as to aid the opening and closing of the garage door 10, in the manner well known to those of ordinary skill in the art.

The wall console 32 is supported on one of the internal sidewalls 34 and enables communication with the barrier operator 20 to provide user-instituted instructions to the controller 30. These instructions are initiated by the depression of different buttons on the console initiating signal communications to the barrier operator 20 respectively representing, for example, door movement commands, work light instructions, and vacation lock mode (set or release). Additional details regarding this operation are subsequently described. The signal communications from console 32 are transmitted to the barrier operator either by way of hardwire conductor means 36, as shown, or alternatively by wireless communication. In similar manner, a keyless entry console (not shown) is in wired or wireless communication with the barrier operator 20 and similarly enables user-instructed instructions to the controller 30.

The barrier operator system 1 illustrated in FIG. 1 may also include one or more types of external entrapment devices, well known to those of ordinary skill in the art, for detecting and effecting a response to obstructions that may be encountered by the door 10 as it is being closed. A first type of such device is disclosed as an elongated sensor strip 38 that is mounted on the lower edge of the door 10 and is operable, upon engagement with an obstruction in the doorway, to transmit a signal to the controller 30 to halt the downward movement of the door 10, typically followed by its return to the open position. A second type of external entrapment device may be an optical assembly 39 comprising an optical beam transmitter 40, typically of the infrared type, disposed on one side of the doorway opening, and a receiver 42 disposed on the opposite side of such opening and positioned to receive the beam 46 from the transmitter 40. This assembly, often referred to as a safety beam or STB, is operable to transmit a signal via conduit 44 (or in some embodiments wirelessly) to the controller 30 to halt the downward movement of the door whenever an obstruction in the doorway opening interrupts the beam 46. Either one, or both, of these external entrapment devices may be used with an internal entrapment approach which is based upon the sensing of a change in motor operation characteristics (e.g., increased torque) due to the engagement of an obstruction, the details of which are subsequently described.

In some embodiments, and as shown in FIG. 1, the barrier operating system 1 includes a sensor 60 for detecting a undesirable condition in the space 54 (such as a garage, warehouse area or other space) at least partially enclosed by the door 10. Instead of, or in addition to, the sensor(s) 60 a water detection sensor 64 may also be used and operatively connected to the controller 30.

The sensor 60 may be used to detect an undesirable condition such as the presence of too much heat, CO, smoke, or other undesirable condition. For example, there may be a threshold amount of heat, CO, smoke or other undesirable condition that the controller 30 may permit but when the threshold amount of an undesirable condition is detected, the controller 30 will take action. In some embodiments, a user may program how what the threshold is. In some embodiments the threshold may be pre-set at time of manufacture. Different thresholds may exist for different substances or conditions.

Actions the controller 30 may take when an undesirable condition is detected may include causing the door 10 to move from a closed position to an open position or at least a partially open position. By opening the door 10, heat, CO, water, smoke, or other undesired condition may be mitigated by venting or draining out the at least partially opened door 10. In some embodiments, the door 10 may only open a few inches to allow venting or draining and yet maintain security of the space 54 enclosed by the door 10 (such as, for example a garage, warehouse, or other space) by not being open enough to allow a person to enter the space 54. In some embodiments, a user may program the barrier operator system 1 to move have the door 10 move to specific position when an undesirable condition is detected. In some embodiments, the door 10 position may be pre-set at time of manufacture. The position the door 10 is moved to may vary depending upon what type of undesirable condition is detected.

Optionally, the controller 30 may take different actions and/or additional actions to partially opening the door 10. For example, the controller 30 may operate a venting system 48 which may be wall mounted, as shown in FIG. 1, or ceiling mounted. Other venting systems 49 may be door 10 mounted. The venting systems 48, 49 may include fans and vent heat, CO, smoke, and other undesirable substances out of the space 54. In some embodiments a drainage system 52

(which may include a pump) can be activated by the controller 30 to drain water or other undesirable liquids out of the space 54. Depending upon the undesirable condition detected, the controller 30 may operate any combination of the door 10, the ventilation systems 48, 49 or a drainage system 52. Once the undesirable condition is not longer detected or no longer is at or above the threshold level, the controller 30 may close the door 10 and/or deactivate the ventilation system 48, 49 and/or the drainage system 52.

Figure 2:
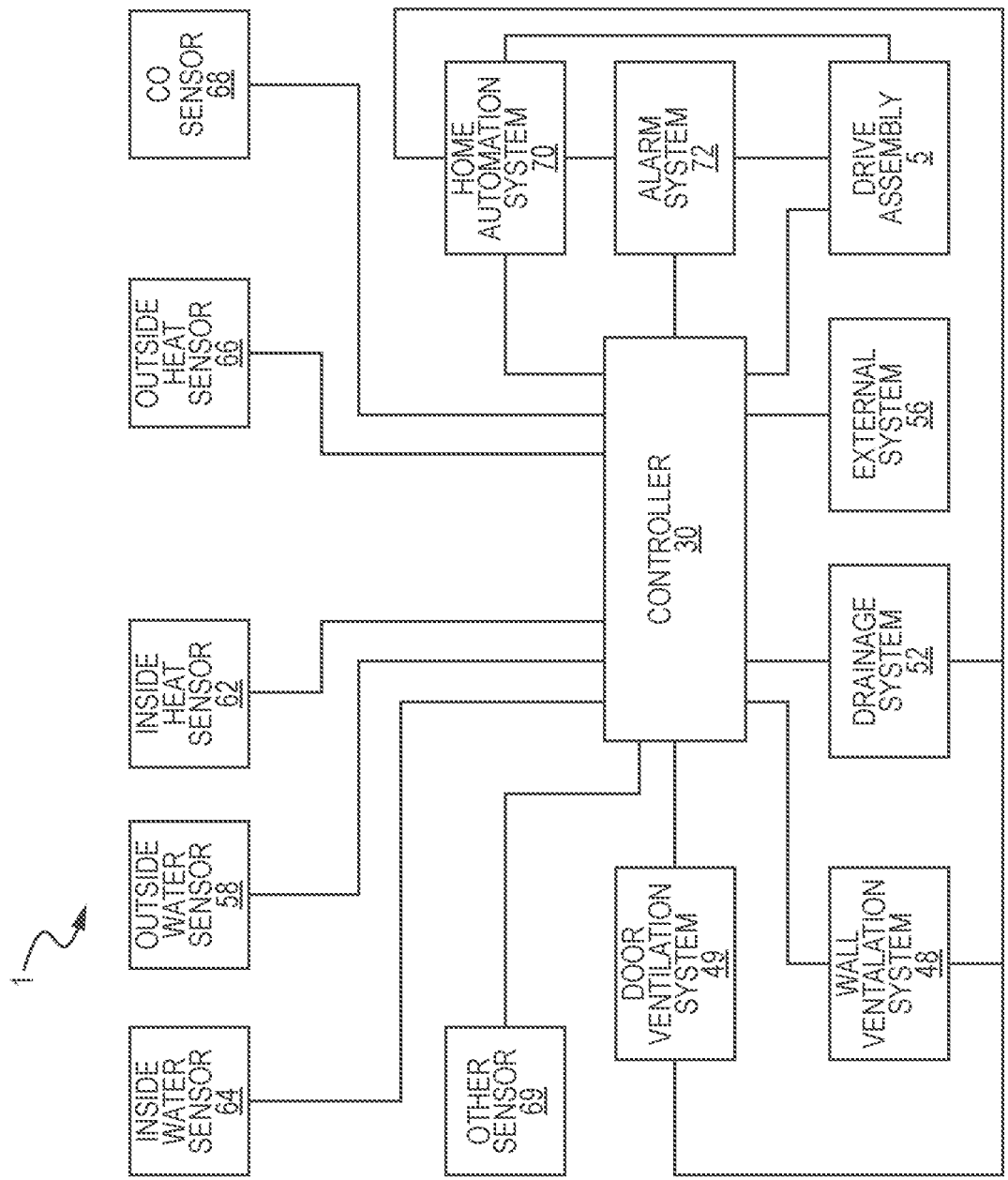
FIG. 2 is a schematic diagram an upward acting door system in accordance with the present disclosure.

FIG. 2 is a schematic diagram an upward acting door system in accordance with the present disclosure. The controller 30 which may be a micro controller, controls the barrier operator system 1. In some embodiments the controller 30 resides in the controller unit or housing 26 shown in FIG. 1. The sensor 60 shown in FIG. 1 may be a combination sensor or multiple sensors. For example, the sensor 60 may in include or be a heat sensor 62, a CO sensor 68 or other sensor 69 (smoke or other sensor for detecting an undesirable condition). The sensor 60, 62, 68, 69 is operatively connected to the controller 30 to indicate to the controller 30 the presence of an undesirable substance or condition. If an undesirable condition is detected or detected to be above a threshold amount the controller 30 is operatively connected to the drive assembly 5 and cause the drive assembly 5 to move the door 10 to an open or at least partially open position.

A liquid sensor 64 can detect the presence of water or other liquid in the space 54 enclosed by the door 10. A user may select the height from the floor 18 (see FIG. 1) the liquid sensor 64 is located in order to set a depth threshold of how deep the liquid is before triggering a signal to the controller 30.

In some embodiments, there is an inside water sensor 64 located inside the space 54 enclosed by the garage door 10 and an outside water sensor 58 both operatively connected to the controller 30. Further, there may be both in inside heat sensor 62 and outside heat sensor 66. In embodiments where there are both inside 62, 64 and outside sensors 58 and 66, the controller 30 may compare readings from the both the inside 62, 64 and outside sensor 58, 66 to ensure that the liquid level and/or heat reading are not greater outside than inside. If the outside sensors 58 and 66 detect a higher reading of a undesirable condition outside than inside the controller 30 will not cause the door 10 to move to an open or partially open system even if the inside sensors 62, 64 detect undesirable conditions in excess of a threshold amount. It will be appreciated that the door 10 is not moved to an open or partially opened position in such instances because there would be no venting of the undesirable condition. Rather, in such cases, opening the door 10 would exacerbate the undesirable condition. Likewise, the CO sensor 68 and other sensors 69 may also operate in inside and outside pairs similar to as described above.

Optionally, the barrier operator system 1 may include ventilation systems 48,49 and or a drainage system 52. The ventilation systems 48, 49 and/ or drainage system 52 are operatively connected to the controller 30. The ventilation systems may be door mounted 49 or wall mounted 48 as described above with respect to FIG. 1. In systems 1 that use ventilation systems 48, 49 and/or drainage system 52, the systems 48, 49, 52 may be activated by the controller 30 when undesirable conditions in the space 52 (see FIG. 1) are detected. If a liquid is detected, the drainage system 52 and/or the door 10 may move to an open or partially open position. If excessive heat, smoke CO or other undesirable condition is detected the ventilation systems 48, 49 may be activated and/or the door 10 may be moved to an open or partially open position. In some embodiments the drainage system 52, ventilation systems 48,49 will be deactivated and the door 10 will be returned to the closed position when the undesired position is no longer detected.

In some embodiments, the barrier operator system may interface with a home automation system 70 (such as but not limited to Amazon Alexia, Google home, etc.). The home automation system 70 is operatively connected to the controller 30 and may be connected wirelessly or by wire. The home automation system 70 may optionally be connected to the drive assembly 5, the drainage systems 52, and the ventilation systems 48, 49 and may operate and/or share data them. Optionally, a home alarm system 72 may be operatively connected to the controller 30 and/or the drive assembly 5 and may operate or control and/or share data with them. In some embodiments, the home automation system 70, the alarm system 72 and the controller 30 may share data with each other.

In some embodiments, if the controller 30 receives a signal(s) indicative of high levels of CO (as to exceed a high level CO threshold which may be programmed by a user or preset at the manufacturer) and/or high levels of smoke (as to exceed a high level smoke threshold which may be programmed by a user or preset at the manufacturer) the controller 30 will send a notification signal to an external system 56 such as local emergency services, a remote monitoring system or other external system. Optionally, the controller 30 may send a notification signal to the alarm system 72 and/or home automation system 70 to alert the occupants of the building in which the space 54 is located so they leave the building, check on the space 54 or otherwise take appropriate action. If a rapid increase in heat and/or smoke is detected by the system, the external system 56, alarm system 72 and/or home automation system 70 may be sent a notification signal as discussed above. Further, in the case of a rapid increase in heat and/or smoke a signal may be sent by the controller 30 to close the door 10.

While the disclosure has been described in terms of exemplary aspects, those skilled in the art will recognize that the disclosure can be practiced with modifications in the spirit and scope of the appended claims. These examples given above are merely illustrative and are not meant to be an exhaustive list of all possible designs, aspects, applications or modifications of the disclosure.

I claim:

1. A door operator comprising:
a controller;
a sensor operatively connected to the controller, the sensor configured to detect an undesirable condition comprising at least one of heat or smoke, and communicate a signal to the controller when the undesirable condition is detected; and
a door operatively connected to the controller, the controller is configured to cause the door to move from a fully closed position to a non-closed position when the controller receives the signal;
wherein the door operator is configured to communicate with a home automation system to provide an alert to occupants that the undesirable condition is present, and wherein the controller is configured to cause the door to return to the fully closed position when the controller receives a signal from the sensor indicating a rapid increase in at least one of heat or smoke.

2. The door operator of claim 1, wherein any one of controller and sensor are configured to cause the door to open when an amount of heat exceeds a threshold amount.

3. The door operator of claim 2, wherein the controller is configured to allow a user to select the threshold amount.

4. The door operator of claim 1, wherein the door is configured to move between the fully closed and a fully open position, and the door moves to an intermediate position between the fully closed and the fully open position and stops at the intermediate position after the controller receives the signal from the sensor.

5. The door operator of claim 4, wherein the controller is configured to move the door from the intermediate position to the fully closed position when the undesirable condition is no longer detected.

6. The door operator of claim 1, further comprising a second sensor operatively connected to the controller, the second sensor configured to detect a second undesirable condition and communicate a second signal to the controller when the second undesirable condition is detected, and the controller is configured to cause the door to move from the fully closed position to the non-closed position when the controller receives the second signal.

7. The door operator of claim 6, wherein the second undesirable condition the sensors are configured to detect is any one of: heat, carbon monoxide, smoke, and a liquid pooled on a floor.

8. The door operator of claim 7, wherein the undesirable condition and the second undesirable condition are different from each other.

9. The door operator of claim 6, further comprising a third sensor operatively connected to the controller, the third sensor configured to detect a third undesirable condition and communicate a third signal to the controller when the third undesirable condition is detected, and the controller is configured to cause the door to move from the fully closed position to the non-closed position when the controller receives the third signal.

10. The door operator of claim 1, further comprising a vent system operatively connected to the controller and configured to be activated by the controller.

11. A method of operating a door comprising:
    detecting an undesirable condition with a sensor, the undesirable condition comprising a liquid pooled within a space enclosed by the door, the sensor being configured to detect a presence of the liquid;
    sending a first signal to a controller when the undesirable condition is detected by the sensor, wherein a threshold depth of the liquid before the first signal is sent is set based on a height of the sensor from a floor of the space enclosed by the door;
    detecting with a second sensor liquid pooled outside the space enclosed by the door;
    sending a second signal to the controller when the liquid pooled outside the space is detected;
    determining that a liquid level outside the space enclosed by the door is less than a liquid level inside the space enclosed by the door based on the first signal; and
    moving the door, in response to the determining, from a closed position to a non-closed position.

12. The method of claim 11, moving the door to an intermediate position between a fully closed and a fully open position and stopping the door at the intermediate position after the determining.

13. The method of claim 11, further comprising moving the door to a closed position when the undesirable condition is no longer detected.

14. The method of claim 11, further comprising sending, in response to the determining, an alert signal to at least one of any one of: an external system, a home automation system, and an alarm system.

15. A door operator comprising:
    a controller;
    a first sensor operatively connected to the controller, the first sensor configured to detect an undesirable condition comprising any one of heat, smoke, liquid, or carbon monoxide and communicate a first signal to the controller when the undesirable condition is detected;
    a second sensor operatively connected to the controller, the second sensor configured to detect the undesirable condition and communicate a second signal to the controller when the undesirable condition is detected; and
    a door operatively connected to the controller;
    wherein the first sensor is disposed within a space enclosed by the door and the second sensor is disposed outside the space enclosed by the door, and wherein the controller is configured to cause the door to move from a closed position to an intermediate position between a fully closed position and a fully opened position and stop at the intermediate position in response to determining a level of the undesirable condition is greater inside the space enclosed by the door than outside the space enclosed by the door, wherein the intermediate position establishes an opening distance which maintains security of a space enclosed by the door by preventing entrance of a person.

16. The door operator of claim 15, wherein the controller is configured to allow a user to determine a location of the intermediate position.

17. The door operator of claim 15, further comprising a vent system operatively connected to the controller and configured to be activated by the controller when the undesirable condition is detected.

18. The door operator of claim 15, further comprising a drainage system, wherein a pump of the drainage system configured to remove liquid from the space enclosed by the door is activated by the controller when liquid is detected by the first sensor.

* * * * *